US007892495B2

(12) United States Patent
Huebner et al.

(10) Patent No.: US 7,892,495 B2
(45) Date of Patent: Feb. 22, 2011

(54) SENSING DEVICE AND METHOD FOR RAPIDLY DETERMINING CONCENTRATIONS OF MICROBIAL ORGANISMS USING INTERFACIAL PHOTO-VOLTAGES

(76) Inventors: Jay S. Huebner, 1 UNF Dr., Jacksonville, FL (US) 32224; Doria F. Bowers, 1 UNF Dr., Jacksonville, FL (US) 32224; Erica N. Mejia, 1 UNF Dr., Jacksonville, FL (US) 32224

( * ) Notice: Subject to any disclaimer, the term of this patent is extended or adjusted under 35 U.S.C. 154(b) by 0 days.

(21) Appl. No.: 12/173,809

(22) Filed: Jul. 15, 2008

(65) Prior Publication Data

US 2009/0221025 A1 Sep. 3, 2009

Related U.S. Application Data

(60) Continuation-in-part of application No. 12/080,880, filed on Apr. 7, 2008, which is a division of application No. 12/074,169, filed on Feb. 29, 2008, and a continuation-in-part of application No. 10/005,717, filed on Nov. 8, 2001, now Pat. No. 7,354,770.

(60) Provisional application No. 60/246,880, filed on Nov. 8, 2000.

(51) Int. Cl.
*B01L 3/02* (2006.01)

(52) U.S. Cl. ......................... 422/100; 422/99; 436/147; 436/151; 436/164; 250/338.3

(58) Field of Classification Search ................. 436/147, 436/151, 164; 422/99–100; 250/338.3
See application file for complete search history.

(56) References Cited

U.S. PATENT DOCUMENTS

| | | | |
|---|---|---|---|
| 4,806,490 | A | 2/1989 | Bischoff et al. |
| 4,883,579 | A | 11/1989 | Humphries et al. |
| 4,892,640 | A | 1/1990 | Wolfbeis et al. |
| 5,074,977 | A | 12/1991 | Cheung et al. |
| 5,108,576 | A | 4/1992 | Malmros et al. |
| 5,328,847 | A | 7/1994 | Case et al. |
| 5,413,915 | A | 5/1995 | Case et al. |
| 5,468,645 | A | 11/1995 | Kirollos et al. |
| 5,500,188 | A | 3/1996 | Hafeman et al. |
| 5,567,302 | A | 10/1996 | Song et al. |

(Continued)

*Primary Examiner*—Jyoti Nagpaul
(74) *Attorney, Agent, or Firm*—Mark Young, P.A.

(57) ABSTRACT

A system for detecting a wide range of microbial organisms, including virus, and determining concentrations in near real-time to determine titer, without the requirement to grow micro-organisms includes an electrometer configured to measure photo-induced interfacial voltages and an electrode assembly with a substrate and at least one electrode on a surface of the substrate electrically coupled to the electrometer. An attachment factor is applied to an exposed surface of each electrode. The attachment factor is effective for interaction with the microbial organism. A transparent vessel for containing the electrolytic solution is provided. The microbial organism may be contained in the electrolytic solution or applied to the coated electrode before being submerged in the electrolytic solution. A light source is configured to controllably produce a flash of activating light directed through the transparent vessel at the electrode causing a sensible photo-induce interfacial voltage indicative of the microbial organism and titer. A corresponding method includes steps of preparing the electrode surfaces with an attachment factor and exposing the submerged electrode surfaces to a flash of activating light to induce interfacial voltages indicative of a determined microbial agent and titer.

7 Claims, 13 Drawing Sheets

U.S. PATENT DOCUMENTS

| | | | |
|---|---|---|---|
| 5,599,717 A | 2/1997 | Vo-Dinh | |
| 5,622,868 A | 4/1997 | Clarke et al. | |
| 5,628,890 A | 5/1997 | Carter et al. | |
| 5,679,535 A | 10/1997 | Joyce et al. | |
| 5,936,730 A | 8/1999 | Foley et al. | |
| 5,938,617 A | 8/1999 | Vo-Dinh | |
| 5,981,287 A | 11/1999 | Sinclair et al. | |
| 6,130,097 A | 10/2000 | Polzius et al. | |
| 7,354,770 B2 * | 4/2008 | Huebner et al. | 436/147 |

* cited by examiner

| Analyte | Attachment factor |
|---|---|
| Micrococci | 5,10,15, 20-Tetrakis(pentafluorophenyl) 21H,23porphine |
| Micrococci | 2-Nitro-5,10,15, 20-tetraphenyl-21H, 23H-porphine copper(II) |
| Micrococci | 5,10,15, 20-Tetraphenyl-21H, 23H-porphine iron (III)chloride |
| E. coli | 5,10,15, 20-Tetraphenyl-21H, 23H-porphine iron (III)chloride |
| Sindbis virus | Heparan sulfate (proteoglycan) |
| Sindbis virus | Polyclonal anti-Sindbis antibody |
| Porcine parvovirus | 5,10,15,20 Tetra (4pyridyl)-21H, 23H porphyrin |
| Porcine parvovirus | 2,3,7,8,12,13,17,18 Octaethylporphinepalladium (II) |

FIGURE 9

Detection of Sindbis virus with anti-SIN coated electrode

- 5E7 SIN PFU/ml
- 5E6 SIN PFU/ml
- 5E5 SIN PFU/ml
- 5E4 SIN PFU/ml
- 1mM NaCl Control

SENSING DEVICE AND METHOD FOR RAPIDLY DETERMINING CONCENTRATIONS OF MICROBIAL ORGANISMS USING INTERFACIAL PHOTO-VOLTAGES

RELATED APPLICATIONS

This application is a continuation in part and claims the benefit of priority of pending U.S. Nonprovisional application Ser. No. 12/080,880, filed Apr. 7, 2008, and pending U.S. Nonprovisional application Ser. No. 12/074,169, filed Feb. 29, 2008, the entire contents of which are incorporated herein by this reference, which are a continuation in part and divisional applications, respectively, that claim the benefit of priority of U.S. Nonprovisional application Ser. No. 10/005,717, filed Nov. 8, 2001, which issued as U.S. Pat. No. 7,354,770 on Apr. 8, 2008, the entire contents of which are incorporated herein by this reference, which claims the benefit of priority of U.S. Provisional Application 60/246,880, filed Nov. 8, 2000, the entire contents of which are incorporated herein by this reference.

GOVERNMENT RIGHTS

This invention was derived from work partially funded by the U.S. Government under Contracts Nos. W011SR-04-C-0072, W011SR-05-C-0043 and W011SR-07-C-099 from the Department of Army, Edgewood Chemical Biological Center, and Grant No. N00014-06-1-0133 from the Department of the Navy, Office of Naval Research. The U.S. Government may have a paid-up license in this invention and the right in limited circumstances to require the patent owner to license others on reasonable terms as provided for by the terms of the Contracts and Grant.

FIELD OF THE INVENTION

This invention generally relates to detection of microbial organisms, and more particularly, to systems and methods for detecting microbial organisms and determining concentrations by measuring interfacial photo-voltages induced by flash illuminations and correlating the measurements with experimental data.

BACKGROUND

Researchers, medical professionals and others must frequently determine the presence and concentration of a large number of different types of microbial organisms, including viruses. Many qualitative and quantitative methods are known in the scientific arts. A number of these methods require either expensive equipment to analyze the test sample, analysis of the sample at a location remote from the sample collection location, or relatively long time periods to produce the result. By way of example, determining titer typically entails serial dilution of a sample followed by culturing, which may take several days. The process is tedious, time consuming and must be carried out in a controlled laboratory environment.

As another example, Coulter counters are frequently used to detect and quantitate microbial organisms by measuring changes in electrical conductance of a small aperture as fluid containing the organisms is drawn through. The solution being studied is drawn with a vacuum pump through an electrically charged tube with a tiny hole at one end. As it passes through the hole, each particle within the solution blocks the electrical field for a moment. Distortions in voltage can be matched to specific types and numbers of particles. One substantial disadvantage of existing Coulter counters is their low throughput efficiency, which substantially extends measurement times. Coulter counting measurement relies on particles passing through a tiny orifice (microchannel) one by one from one chamber to the other. Thus, in order to complete sampling of a small number of particle solutions, thousands of micro or nanoparticles have to pass through the orifice one by one, which could be prohibitively time consuming. As another disadvantage, the equipment is costly. Furthermore, while the Coulter counter is effective for counting prokaryotic (bacterial) cells, it is not useful for counting virus because of their much smaller size.

As yet another example, some methods determine the presence of an analyte, but provide no information about the concentration. Illustratively, the "presence/absence" format of bacterial testing, such as in the Colilert® chemical mixture (IDEXX, Laboratories, ME) test, detects the presence of the targeted organism (e.g., fecal coliforms) but give no idea as to microbe concentrations. Colilert® also requires incubation in test water for 24 hours before results can be obtained.

What is needed is a simple, cost effective and reliable system and method for detecting a wide range of microbial organisms, including virus, and determining concentrations in near real-time to determine titer, without the requirement to grow micro-organisms. The invention is directed to overcoming one or more of the problems and solving one or more of the needs as set forth above.

SUMMARY OF THE INVENTION

To solve one or more of the problems set forth above, in an exemplary implementation of the invention, a simple, cost effective and reliable system and method for detecting a wide range of microbial organisms, including virus, and determining concentrations in near real-time to determine titer, without the requirement to grow micro-organisms is provided. In one aspect of an exemplary implementation of a system according to principles of the invention, an apparatus for detecting the presence and concentration of a microbial organism in an electrolytic solution through measured photo-induced interfacial voltages is provided. The apparatus includes an electrometer configured to measure photo-induced interfacial voltages and an electrode assembly comprising a substrate and at least one electrode on a surface of the substrate electrically coupled to the electrometer. An attachment factor is applied to an exposed surface of each electrode. The attachment factor is effective for interaction with the microbial organism. A transparent vessel for containing the electrolytic solution with the microbial organism is provided. The electrode assembly is configured for placement of each electrode in the transparent vessel. A light source is configured to controllably produce a flash of activating light directed through the transparent vessel at the electrode. The flash of activating light causes a sensible photo-induce interfacial voltage at each electrode when the electrode with the applied attachment factor is exposed to the flash of activating light while submerged in the electrolytic solution containing the microbial organism. The light source is preferably a source of ultraviolet light and the flash of activating light is a flash of ultraviolet activating light. The electrodes are preferably platinum, although other conductive materials may be used. A plurality of electrodes and at least one ground may be provided on the electrode assembly. The electrometer may include an amplifier and a processor operably coupled to the electrode assembly. The processor may be configured to compare a measured photo-induced interfacial voltage with a predetermined photo-induced interfacial voltage corresponding to a determined analyte and titer. The microbial organism may be a virus, although other microbial organisms may be detected and quantitated in addition to or in lieu of a virus. The electrode assembly produces and the electrometer is configured to measure photo-induced interfacial voltages (e.g., +10 to −10 mV) in less than 500 μs after exposure to the flash of activating light.

In another aspect of an exemplary implementation of a system according to principles of the invention, an apparatus for detecting the presence and concentration of a microbial organism applied to an electrode before being submerged in an electrolytic solution through measured photo-induced interfacial voltages is provided. The apparatus includes an electrometer configured to measure photo-induced interfacial voltages and an electrode assembly comprising a substrate and at least one electrode on a surface of the substrate. Each electrode is electrically coupled to the electrometer. A thin film of tissue culture adhesive is applied to the exposed electrode surface. An attachment factor is applied to the thin film on the exposed surface of each electrode. The attachment factor is effective for interaction with the microbial organism. The electrode with the thin film and attachment factor is then exposed to a microbial organism, which interact with the attachment factor. A transparent vessel contains an electrolytic solution. The electrode assembly with the thin film, attachment factor and interacted microbial organism is configured for placement in the transparent vessel. A light source is configured to controllably produce a flash of activating light (e.g., UV light) directed through the transparent vessel at the electrode. The flash of activating light causes a sensible photo-induce interfacial voltage at the at least one electrode when the at least one electrode with the applied thin film, attachment factor and microbial organism is exposed to the flash of activating light while submerged in the electrolytic solution. The electrodes are preferably platinum, although other conductive materials may be used. A plurality of electrodes and at least one ground may be provided on the electrode assembly. The electrometer may include an amplifier and a processor operably coupled to the electrode assembly. The processor may be configured to compare a measured photo-induced interfacial voltage with a predetermined photo-induced interfacial voltage corresponding to a determined analyte and titer. The microbial organism may be a virus, although other microbial organisms may be detected and quantitated in addition to or in lieu of a virus. The electrode assembly produces and the electrometer is configured to measure photo-induced interfacial voltages (e.g., +10 to −10 mV) in less than 500 μs after exposure to the flash of activating light.

A method for detecting the presence and concentration of a microbial organism through a measured photo-induced interfacial voltage is also provided. In one aspect of a method according to principles of the invention, an exposed surface of an electrode is coated with an attachment factor. The coated electrode surface is exposed to a microbial organism and submerged in an electrolytic medium. A UV activating light is flashed and emitted UV light is directed through the electrolytic medium at the submerged coated electrode surface. A photo-induced interfacial voltage is produced at the electrode and measured. The measured photo-induced interfacial voltage is associated with a determined photo-induced interfacial voltage for a determined analyte and a determined titer. In one implementation, the microbial organism is contained in the electrolytic medium and the coated electrode surface is exposed to the microbial organism upon submerging the coated electrode surface in an electrolytic medium. In another implementation, the microbial organism is applied to the coated electrode surface before submerging the coated electrode surface in an electrolytic medium.

BRIEF DESCRIPTION OF THE DRAWINGS

The foregoing and other aspects, objects, features and advantages of the invention will become better understood with reference to the following description, appended claims, and accompanying drawings, where:

FIG. 9 is a table of attachment factors for use in detecting specific microbial organisms and determining concentrations by measuring interfacial photovoltages induced by flash illuminations according to principles of the invention.

The photovoltages graphically illustrated in FIGS. 10 through 16 are amplified interfacial photovoltages that were output from electrodes and then amplified by an electrometer with a gain of about 10.

Those skilled in the art will appreciate that the figures are not intended to be drawn to any particular scale; nor are the figures intended to illustrate every possible embodiment, analyte, attachment factor, system component, or methodology step of the invention. The invention is not limited to the exemplary embodiments or experimental data depicted in the figures.

DETAILED DESCRIPTION

This invention allows tests to be performed in near real-time to determine titer, without the requirement to grow micro-organisms, which can require one to several days. This current technology allows the user to simply take a sample (potable water source or lab stock culture) and use dilutions of the sample for quantification in a photo-electric titer meter. The photo-electric titer meter (i.e., titer meter) allows for a very rapid, comprehensive microbe test of aqueous solutions. Identification and quantification can be achieved with one device in a less than an hour, and near real-time.

Figure 1:
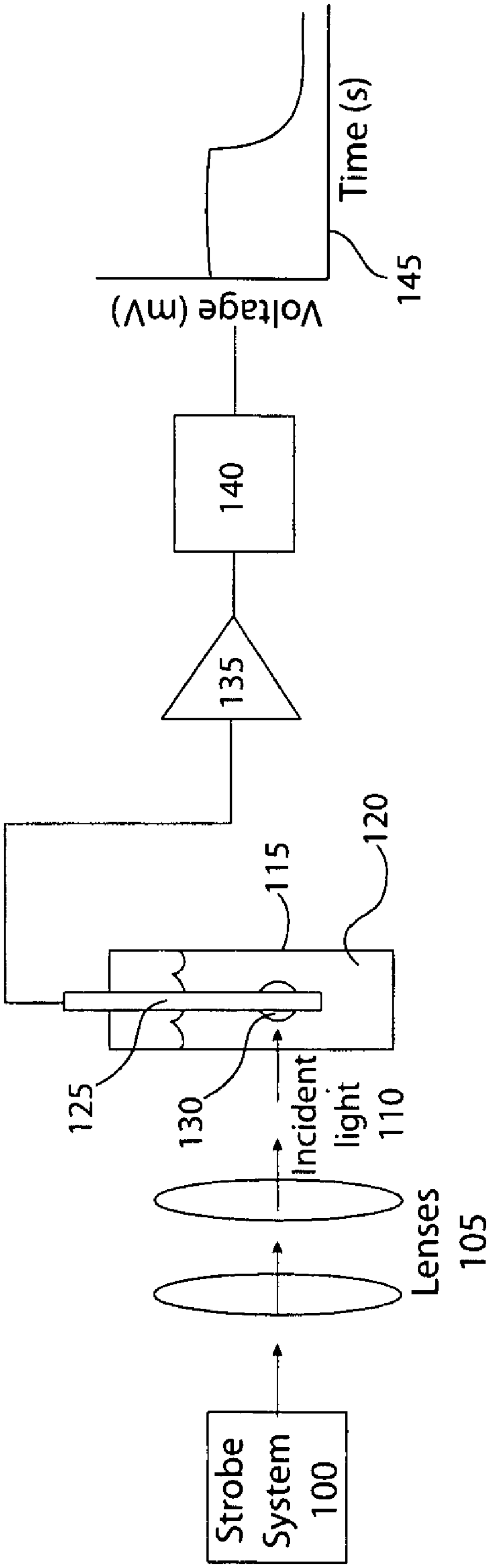
FIG. 1 is a high level schematic of an exemplary system for detecting microbial organisms and determining concentrations by measuring interfacial photo-voltages induced by flash illuminations according to principles of the invention.

Referring to FIG. 1, a high level schematic of an exemplary system for detecting microbial organisms and determining concentrations by measuring interfacial photo-voltages induced by flash illuminations according to principles of the invention is shown. A light source such as an ultraviolet (UV) strobe light 100 provides activation energy in the form of pulses or controllable flashes of light 110. One or more optical elements, such as lenses 105, filters, and beam splitters direct and concentrate the light 110 on one or more electrodes 130 of an electrode assembly 125 in a transparent vessel 115 containing a transparent electrolytic solution 120. In one implementation, the electrolytic solution 120 contains an analyte (i.e., a constituent to be determined using the system), particularly a microbial organism such a virus or bacteria. The electrodes 130 are coated with an attachment factor prior to immersion in the electrolytic solution 120 and exposure to the flash of light. As discussed more fully below, the attachment factor is a substance, such as one or more types of antibodies, selected to attract and bind the analyte. The electrode assembly 125 is electrically coupled to an electrometer 135, which includes an amplifier or gain. The electrometer 135 is operably coupled to processing circuitry and/or equipment 140, i.e., a digitizer, which can be a digital oscilloscope configured to display voltage time traces. The electrometer 135 magnifies input photo-voltages induced by flash illumination of the coated electrode immersed. The amplified photovoltage output, which indicates the type and concentration of analyte, is processed for analysis (as in the graphical display conceptually illustrated at 145) or populating a data store. The processing equipment (i.e., electrometer) may include an oscilloscope able to average signals and compensate for or subtract noise traces. The electrometer may include operational amplifiers configured to cancel radio frequency noise induced in proximate pulsed light sources by using a pair of electrodes, one sensing the photo-voltage induced signals and the other monitoring a baseline electrode assembly not exposed to the analyte.

By way of example and not limitation, the flash light source 100 may be comprised of a pulsed tuneable laser, a xenon stroboscope or, preferably, high intensity LEDs. The light source 100 may be controlled by a switch or light trigger configured to controllably energize the light source and/or by controllably opening a shutter, upon which light is allowed to pass. Depending upon the particular analyte and attachment factor, infrared, visible or ultraviolet light may be emitted. However, for detecting microbial organisms and determining concentrations by measuring interfacial photo-voltages induced by flash illumination, ultraviolet light is preferred.

Optionally, light 110 emitted from the light source 100 may be split and directed simultaneously to a plurality of electrodes 130. By way of example, light may be directed simultaneously to an electrode that is coated with an attachment factor and is submerged in an electrolytic solution containing an analyte, and to another electrode that is coated with the attachment factor and is submerged in the electrolytic solution without the analyte. The electrode in the electrolytic solution without the analyte may be used to establish a baseline or a control output. Alternatively, the second electrode may be submerged in the electrolytic solution with the analyte to provide redundancy and averaging. As yet another alternative, the second electrode may have a different attachment factor and may be submerged in the same electrolytic solution with the analyte or another analyte to test for the presence and concentration of different analytes simultaneously.

Attachment factors absorbed or coated on the surface of an electrode generate transient electrical signals known as photo-induced charge movements (PICM) upon flash illumination. In many circumstances the PICM electrical signals generated by an attachment factor are modified by the presence of other substances (i.e., analytes) in such ways that the presence of these other substances can be detected and their amount determined by analyzing the difference in PICM between a target solution containing the analyte and a control solution which does not contain the analyte.

Figure 2:
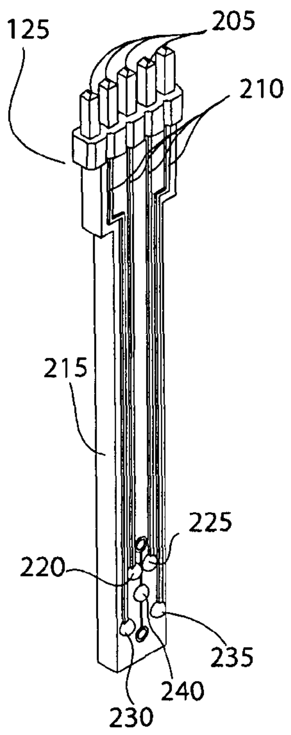
FIG. 2 conceptually illustrates an exemplary electrode assembly for a system for detecting microbial organisms and determining concentrations by measuring interfacial photo-voltages induced by flash illuminations according to principles of the invention.

Referring now to FIG. 2, an exemplary electrode assembly 125 is conceptually illustrated. The exemplary assembly comprises an insulating or dielectric substrate 215 with a plurality of conductive sensing electrodes 220, 225, 230, 235 formed on a surface of the substrate 215. The opposite side of the electrode assembly 125 is comparable to (e.g., the same or substantially the same as) the side that is shown in the Figures. These electrodes 220, 225, 230, 235 define the area where light is directed to measure photo-induced charge movements. The substrate 215 may, for example, comprise a printed circuit board substrate or any other insulating or dielectric material compatible with the electrolytic solution 120. Conductive electrical pathways 210, i.e., leads or traces, extend from each conductive sensing electrodes 220, 225, 230, 235 and a ground 240 to an electronic connector such as one or more terminals of a pin strip 205. The leads 210 are covered with an insulator (e.g., a layer of epoxy) that is compatible with the electrolytic solution 120. The pin strip 205, or other connector, may releasably connect the electrode assembly 125 to the electrometer 135 and/or other circuitry comprising the system.

The conductive sensing electrodes 220, 225, 230, 235 are preferably comprised of platinum (Pt) dot-like structures. However, any other conductive materials responsive to photo-induced charge movements and having the capability to associate chemically with, attach or chemisorb an attachment factor, may be utilized and are intended to come within the scope of the invention. Such other conductive materials may, for example, include gold, aluminum, silver or copper. In another embodiment the electrode may comprise of conducting glass electrodes, for example, Indium tin oxide (ITO) or Tin dioxide, $SnO_2$.

One or more grounds 240 are provided on the electrode assembly 125. The ground 240 provides a reference point from which photo-induced voltages can be measured. Additionally, the ground reduces crosstalk, i.e., a phenomenon by which undesired capacitive coupling causes a signal or voltage transmitted on one channel to have an undesired effect in another channel.

While four conductive sensing electrodes 220, 225, 230, 235 are shown, any electrode configurations having at least one conductive sensing electrode may be utilized and are intended to come within the scope of the invention. By way of example, an exemplary electrode assembly 125 may have one to sixteen or more electrodes, with an even number of electrodes being preferred. Each electrode should be subjected to the incident light 110. There are limits as to how small the electrodes can be and still retain sufficient analyte to produce a sensible and reliable PICM. Concomitantly, the larger the electrode patterns are the more the light from the flash must be spread out which tends to dim the light received by each electrode, and lowers the signal. In experimental testing, good results have been achieved with four electrodes.

Figure 3:
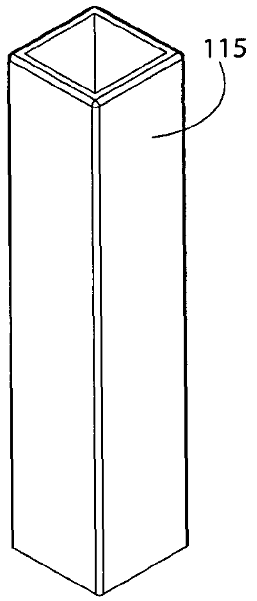
FIG. 3 conceptually illustrates an exemplary cuvette for a system for detecting microbial organisms and determining concentrations by measuring interfacial photo-voltages induced by flash illuminations according to principles of the invention.
Figure 4:
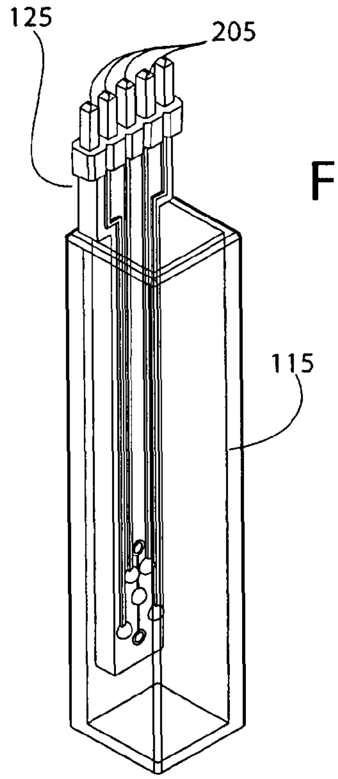
FIG. 4 conceptually illustrates the exemplary electrode assembly in the exemplary cuvette for a system for detecting microbial organisms and determining concentrations by measuring interfacial photo-voltages induced by flash illuminations according to principles of the invention.

Now referring to FIG. 3, a transparent vessel 115, such as a cuvette, is shown. The cuvette 115 may be made of plastic, glass, or optical grade quartz and designed to hold the electrolytic solution 120. At least one side is transparent, allowing UV and visible light to pass through. The cuvette may be open to the atmosphere on top or have a cap to seal it shut. A median wall may extend fully or partially up inside, dividing the interior into two separate compartments so that measurements can be taken with two solutions separated. As shown in FIG. 4, the cuvette 115 is sized to receive the electrode assembly 125.

Figure 5:
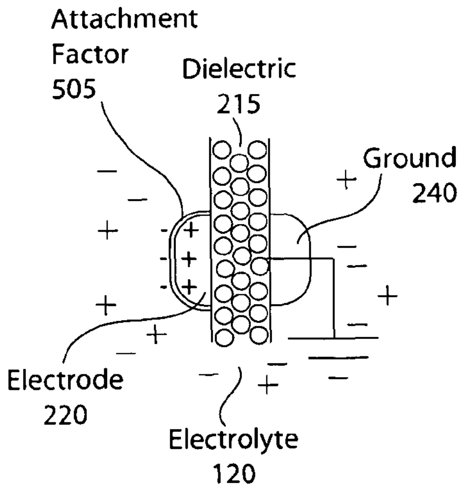
FIG. 5 is a high level schematic of an exemplary electrode assembly coated with an attachment factor in an electrolyte solution for a system for detecting microbial organisms and determining concentrations by measuring interfacial photo-voltages induced by flash illuminations according to principles of the invention.

Referring now to FIG. 5, a high level schematic of a section of an exemplary electrode assembly having an electrode 220 coated with an attachment factor 505 in an electrolyte solution 120 according to principles of the invention is shown. Electrode 220 represents a typical electrode, such as any of the sensing electrodes 220, 225, 230, 235 shown in FIG. 2. A thin layer of a photo-voltage active material, or attachment factor 505, is placed on the electrode 220 so that metal ions in the surrounding electrolytic solution 120 react with it and cause a charge movement. Any of a variety of attachment factors 505 may be utilized. The attachment factor 505 is thin so it does not block transmission of the signal through to the electrode 220. The attachment factor 505 must, of course, also be water-insoluble. A transient charge movement and a proportional photo-voltage can be detected based on interaction of the attachment factor 505 with an analyte in the electrolytic solution 120. The electrode 220 (e.g. an attachment factor coated platinum dot) which the light strikes is the site of the PICM activity. Photo-induced charge movements there generate interfacial photo-voltages which are applied to electrometer input via electrical pathways 210 and are referenced to ground 240 via the electrolyte 115. The PICM in the illustrated example in FIG. 5 makes the electrical potential input to the electrometer 135 positive. Skilled artisans will appreciate that this phenomena is not limited to this polarity, but other attachment factors and microbes will result in the PICMs producing the opposite polarity.

An exemplary electrolytic solution is formed by adding a salt, such as table salt, NaCl, to a solvent such as water. The individual components dissociate due to the thermodynamic interactions between solvent and solute molecules, in a process known as solvation. When the electrolyte, e.g., NaCl, dissolves in the water, the solution will better conduct an electric current. The electrolytic solution thus behaves as an electrically conductive medium.

Figure 6:
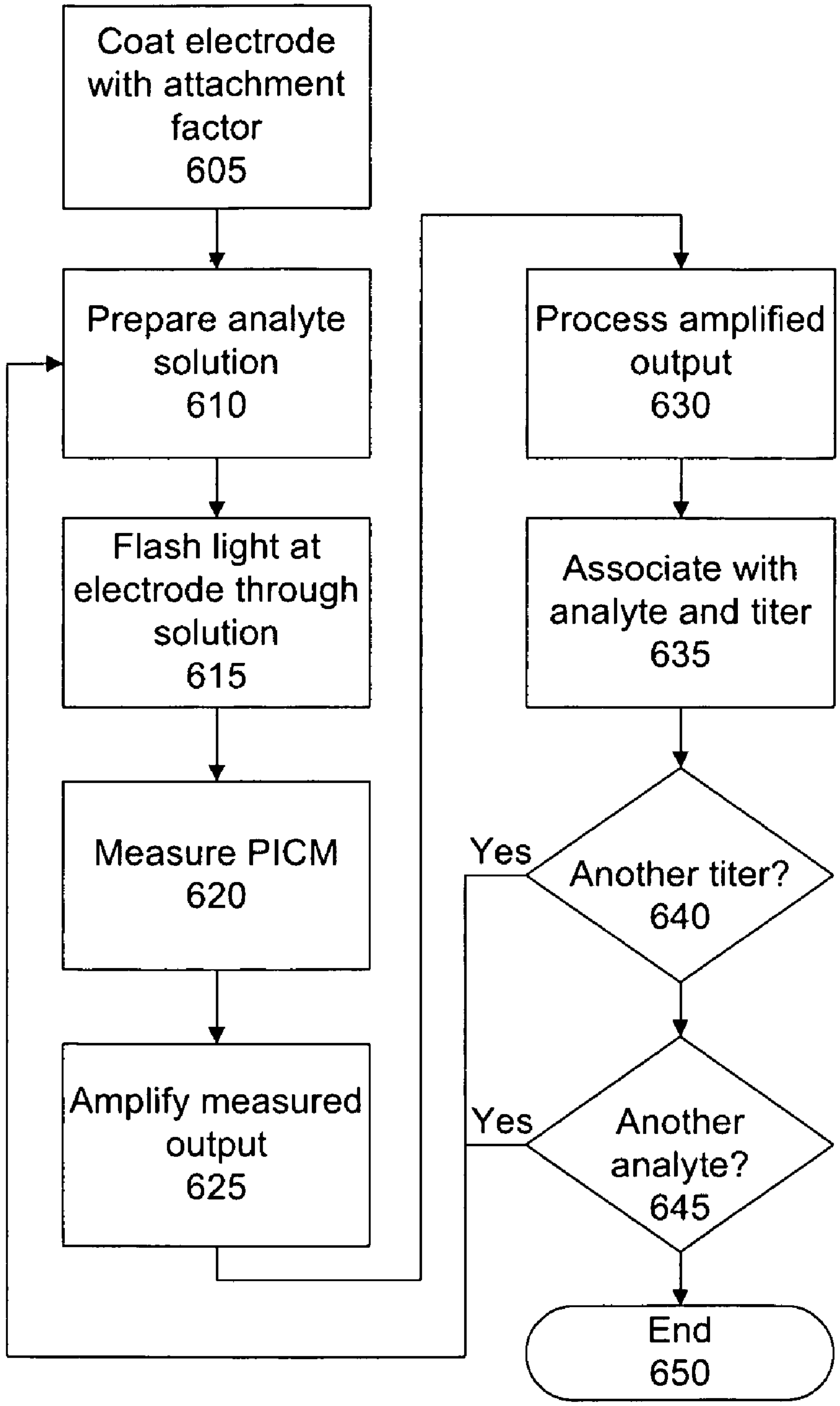
FIG. 6 is a high level flowchart of an exemplary method for determining interfacial photo-voltages induced by flash illuminations for concentrations of microbial organisms according to principles of the invention.

Now referring to FIG. 6, a high level flowchart of an exemplary method for determining interfacial photo-voltages induced by flash illuminations for determining concentrations of microbial organisms according to principles of the invention is shown. Initial steps entail preparation of the electrode and solution. In step 605, the electrode is coated with an attachment factor. By way of example, coating may be performed, for example, by submersion of the electrode in the attachment factor for a determined period of time and under determined conditions. Other coating techniques may include conversion coating, ink jet printing, vapor deposition, spraying, sputtering, vacuum deposition, and any other compatible coating or film forming technique that is now known to skilled artisans or hereafter developed and produces an effective attachment factor coating. An electrolytic solution containing a known concentration of a known analyte is then prepared, as in step 610. With the electrode submerged in the solution, an activating light source is flashed, thereby emitting a pulse of light directed at the electrode, as in step 615. Photo-induced charge movements in the form of interfacial photo-voltages are measured, as in step 620. The interfacial photo-voltages may be measured for a determined period of time. Detected interfacial photo-voltages are amplified in step 625 and processed in step 630. Processing may include digitizing, filtering and otherwise converting the amplified output to useful data. The measured interfacial photo-voltage data is associated with the specific analyte and titer (i.e., concentration) in step 635. The process may be repeated for various concentrations of an analyte, as in step 640. Additionally, the process may be repeated for various analytes, as in step 645. The exemplary process ends, as in step 650, when targeted analytes and titers have been tested. The collected data may subsequently be used to determine whether a particular analyte is present and, if so, in what concentration, by correlating measured interfacial photo-voltages with an analyte and the predetermined corresponding titer. Stored data may include voltage data at discrete time points in the voltage trace, maximum voltage amplitudes, and any other information or constraints (e.g., angular, curvature and end condition information) may be determined to accurately represent a voltage trace.

Figure 7:
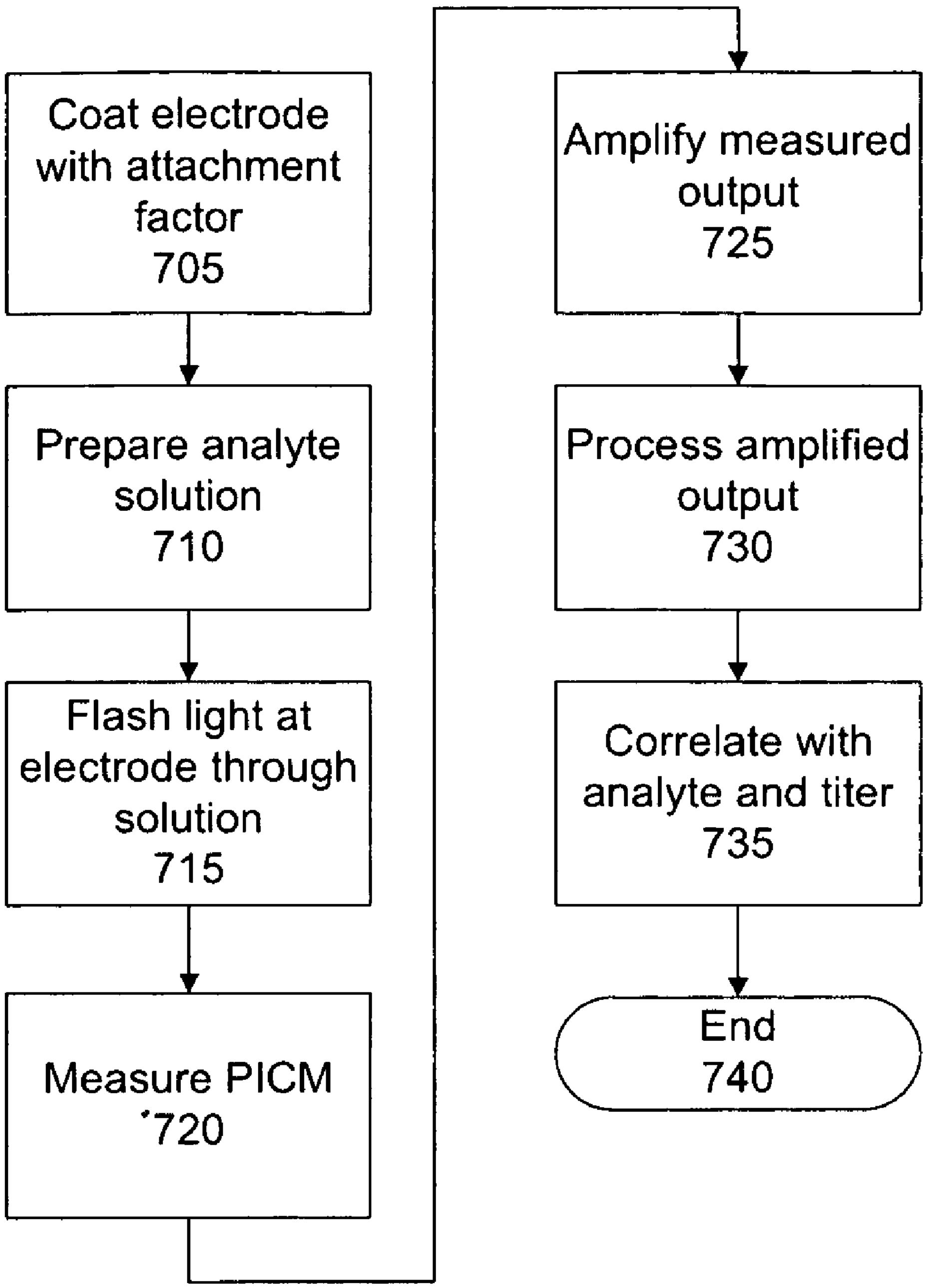
FIG. 7 is a high level flowchart for a method for detecting microbial organisms and determining concentrations by measuring interfacial photo-voltages induced by flash illuminations according to principles of the invention.

Referring now to FIG. 7, a high level flowchart for a method for detecting microbial organisms and determining concentrations by measuring interfacial photo-voltages induced by flash illuminations according to principles of the invention is shown. In step 705, the electrode is coated with an attachment factor. By way of example, coating may be performed by submersion of the electrode in the attachment factor for a determined period of time and under determined conditions. The attachment factor is selected for binding or interaction with one or more analytes. An electrolytic solution suspected of containing an analyte is then prepared, as in step 710. With the electrode submerged in the solution, an activating light source is flashed, as in step 715, thereby emitting a pulse of light directed at the electrode. Photo-induced charge movements in the form of interfacial photo-voltages are measured, as in step 720. The interfacial photo-voltages may be measured for a determined period of time. Detected interfacial photo-voltages are amplified in step 725 and processed in step 730. Processing may include digitizing, filtering and otherwise converting the amplified output to useful data. The measured interfacial photo-voltage is correlated with a specific analyte and titer (i.e., concentration) in step 735. This step may entail determining an analyte and titer from a look-up table, database or other data source that contains predetermined data, such as data determined in accordance with the method of FIG. 6. Interpolation and extrapolation may be used to estimate titer between or beyond available data points. The exemplary process ends, as in step 740, at which time an analyte and titer have been determined from the measured interfacial photo-voltage for the attachment factor.

Figure 8:
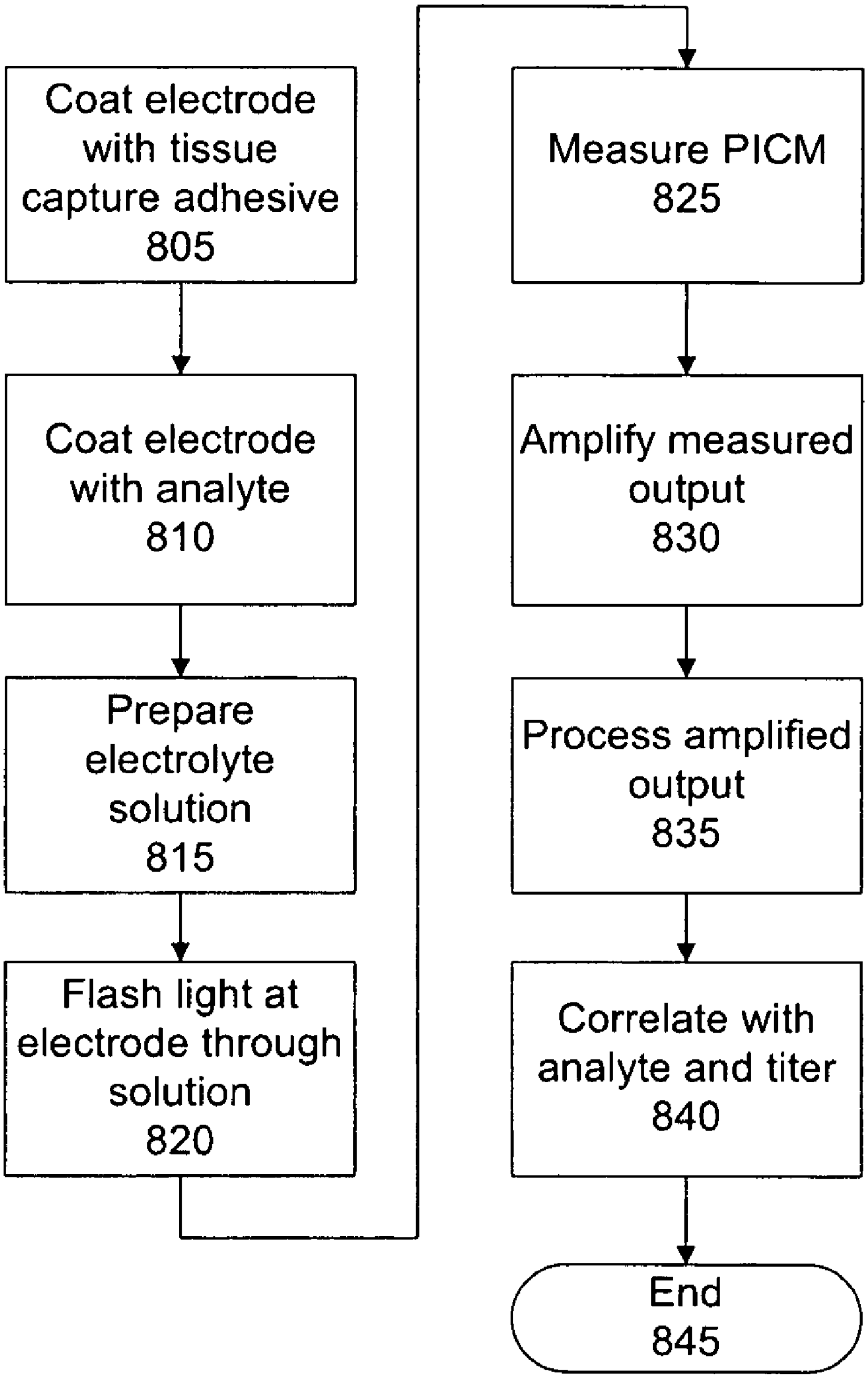
FIG. 8 is a high level flowchart for an alternative method for detecting microbial organisms and determining concentrations by measuring interfacial photo-voltages induced by flash illuminations according to principles of the invention.

Referring now to FIG. 8 is a high level flowchart for an alternative method for detecting microbial organisms and determining concentrations by measuring interfacial photo-voltages induced by flash illuminations according to principles of the invention is shown. In step 805, the electrode is coated with a tissue capture adhesive, such as an adhesive film from a tissue capture pen, and then an antibody is applied to the tissue capture adhesive layer. Tissue capture pens and the thin layer of tissue capture adhesive applied by such devices are well known in the art of microscopy. An analyte may then be physically applied to the coated electrode, such as by submersion, swabbing or other physical contact, as in step 810. An electrolytic solution is then prepared, as in step 815. With the electrode submerged in the solution, an activating light source is flashed, as in step 820, thereby emitting a pulse of light directed at the electrode. Photo-induced charge movements in the form of interfacial photo-voltages are measured, as in step 825. The interfacial photo-voltages may be measured for a determined period of time. Detected interfacial photo-voltages are amplified in step 830 and processed in step 835. Processing may include digitizing, filtering and otherwise converting the amplified output to useful data. The measured interfacial photo-voltage is correlated with a specific analyte and titer (i.e., concentration) in step 840. This step may entail determining an analyte and titer from a look-up table, database or other data source that contains predetermined data, such as data determined in accordance with the method of FIG. 6. Interpolation and extrapolation may be used to estimate titer between or beyond available data points. The exemplary process ends, as in step 845, at which time an analyte and titer have been determined from the measured interfacial photo-voltage for the attachment factor.

Thus, a method of detecting and quantitating an analyte may be carried out by one of two modes to be referred to herein as the "indirect mode" in which the analyte is provided in the electrolytic medium (FIG. 7) and the "direct mode" in which the analyte is applied directly to the electrode assembly (FIG. 8). Application of the analyte to the electrode may be performed remote from the testing apparatus in the direct mode. Thus, for example, a large volume of test media (e.g., water from a pond or reservoir) may be sampled on site remote from the test apparatus.

Referring now to FIG. 9, a table of exemplary attachment factors that have been found effective for use in detecting specific microbial organisms and determining concentrations by measuring interfacial photovoltages induced by flash illuminations according to principles of the invention is provided. The exemplary attachment factors are water-insoluble substances suitable for applying on an electrode and selected to attract one or more specific analytes to facilitate detection and quantitating. Skilled artisans will appreciate that the invention is not limited to the attachment factors or analytes listed in the table. Rather, other attachment factors that interact with a targeted analyte may be utilized so long as it is water-insoluble, suitable for coating on an electrode and enables photo-induced charge movement resulting in an interfacial photo-voltage.

Experimental setups which function as photo-electric microbe sensors were assembled from both commercial and custom designed and manufactured devices. A Perkin Elmer PS-1120 pulsed xenon lighting system with an external 7.5 microfarad capacitor, a control switch and a flash control circuit, with an FX-1154 xenon flashlamp was used as the strobe system 100. A single channel, guarded DIP, ultra low input bias current instrumentation operational amplifier (e.g., INA116PA by Texas Instruments, Inc.) was used. A four channel electrometer 135 was made using a TL084 quad JFET-input operational amplifier. A Tektronix TDS 2014 four channel digital storage oscilloscope with TDS2CM port that supports GPID (IEEE) interface bus communications to a Dell Inspiron 9300 notebook computer running a LabView® application to archive, print and recover the photovoltage data, comprised the digitizer/processor 140. A flash control circuit comprising TTL DIP (7400 series) digital integrated circuits was used to initiate and control strobe flashes. The digital oscilloscope was triggered by and on the bright flashes. A grounded metal box served as a Faraday cage where the cuvette 150, electrode 125, test solution 120 and electrometer 135 were housed.

The invention is not limited to a setup comprised of these elements. Indeed, the aforementioned experimental setup is intended to represent a broad category of systems capable of: (a) controllably flashing a UV light at a vessel containing an electrolytic medium and an electrode coated with an attachment factor that is selected to interact with an analyte; (b) receiving flash induced interfacial photovoltages; and (c) associating data that represents the photovoltages with a particular analyte and titer, in accordance with the present invention. Of course, the system may include fewer, different and/or additional elements, provided it is capable of performing functions in accordance with the present invention as described herein.

Figure 10:
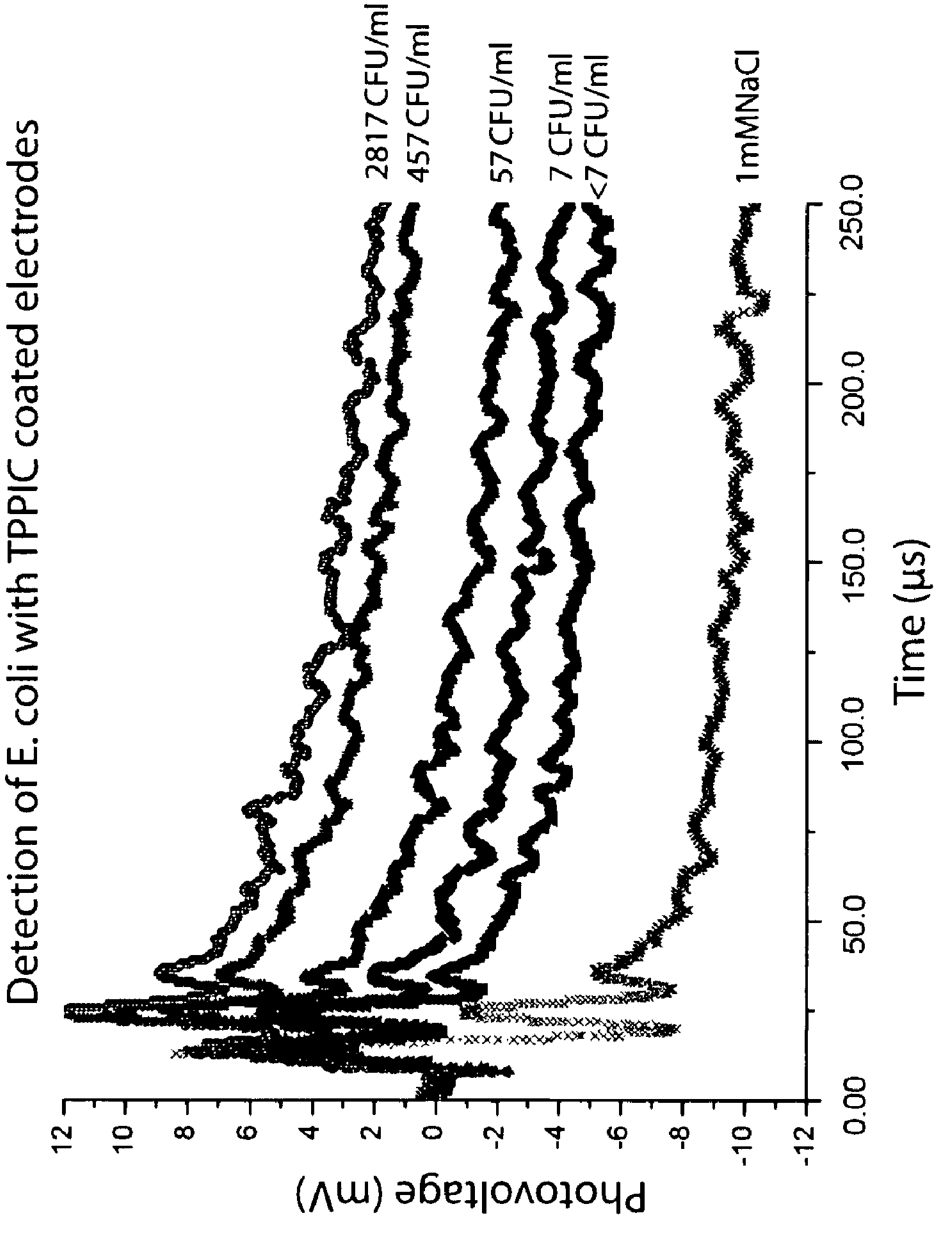
FIG. 10 is a graph showing photovoltage traces for an electrode coated with 5,10,15,20-Tetraphenyl-21H,23H-porphine iron (III)chloride (TPPIC) subsequently exposed to increasing concentrations (i.e., colony forming units [CFU] per milliliter) of *E. coli* in test solutions of 1 mM NaCl according to principles of the invention.

FIGS. 10 through 16 are graphs that illustrate tests performed in accordance with principles of the invention. Specifically, FIG. 10 is a graph showing photovoltage traces for an electrode coated with 5,10,15,20-Tetraphenyl-21H, 23H-porphine iron (III)chloride (TPPIC) subsequently exposed to increasing concentrations (i.e., colony forming units [CFU] per milliliter) of *E. coli* in test solutions of 1 mM NaCl according to principles of the invention. As shown, all photovoltages include initial oscillations from radio frequency noise known to skilled artisans, and after the first 50 μs are initially negative with only 1 mM NaCl present. However, after the initial 50 μs, these traces become increasingly positive with increased *E. coli* titer. The non-linear response to the *E. coli* titer is predicted by models which predict saturation of these effects when most of the attachment factor sites are occupied with microbes. It is possible that some of the responses, particularly at low titer, are partially caused by non-viable *E. coli* cells.

Figure 11:
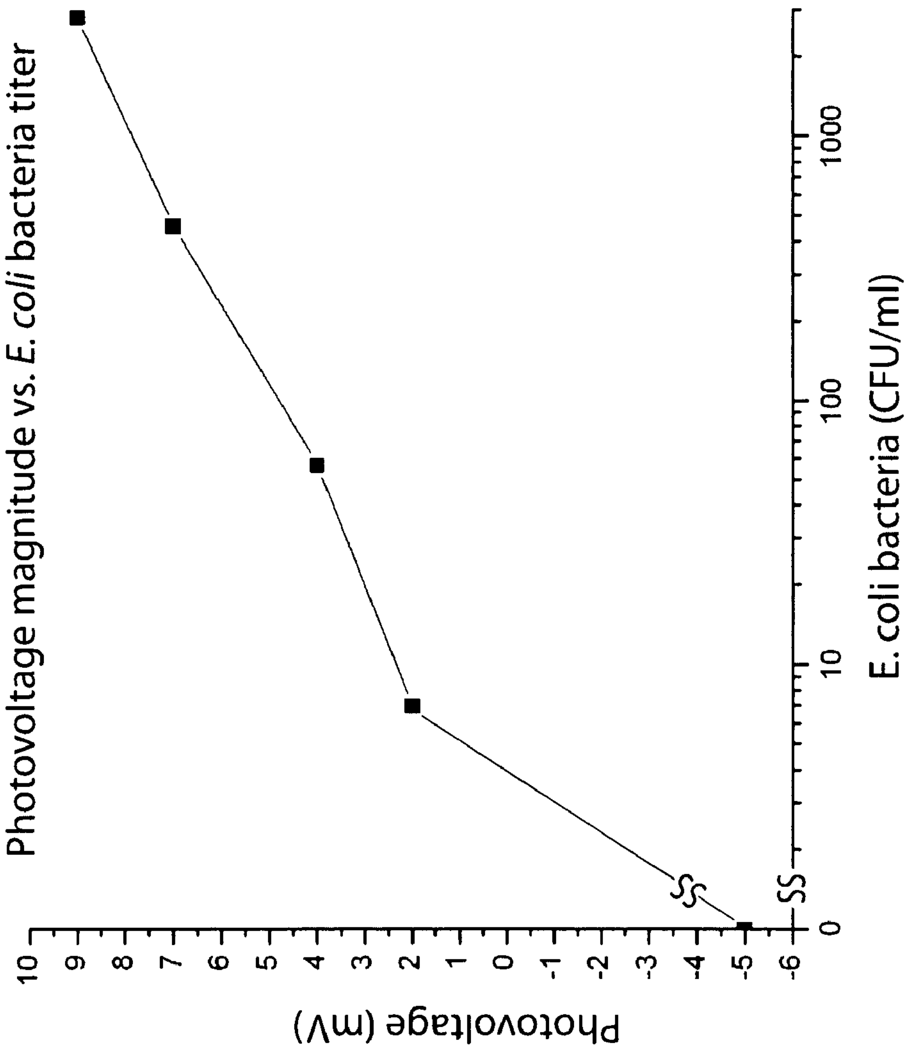
FIG. 11 is a graph showing photovoltage magnitude against *E. coli* concentration for an electrode coated with TPPIC subsequently exposed to increasing concentrations of *E. coli* in test solutions of 1 mM NaCl according to principles of the invention.

FIG. 11 is a graph showing photovoltage magnitude against *E. coli* concentration for an electrode coated with TPPIC subsequently exposed to increasing concentrations of *E. coli* in test solutions of 1 mM NaCl according to principles of the invention. Although a log format is used for the graph, titer value for the left-most point (i.e., the point closest to the ordinate) is zero. Therefore, the line extending from that left-most point and the abscissa are broken and an initial numerical value of 1 on the logarithmic abscissa is replaced with a zero. As shown, photovoltages become increasing positive after the initial RF induced noise with increased *E. coli* titer. The non-linear response is believed to be due to saturation of the attachment factor sites with *E. coli.* This allows sensing equipment to be adapted to sense a relatively narrow range of photovoltages (e.g. from −10 to +10 mV) to be used for a wide range of analyte concentrations and for a wide range of analyte-attachment factor combinations. Shorter exposure times for this attachment factor would alter shift the scale to higher concentrations, while longer exposure times or exposure to larger volumes of test solutions would shift the scale to lower concentrations. Of course, other attachment factors with different binding constants or a larger number of binding sites may also be found.

Figure 12:
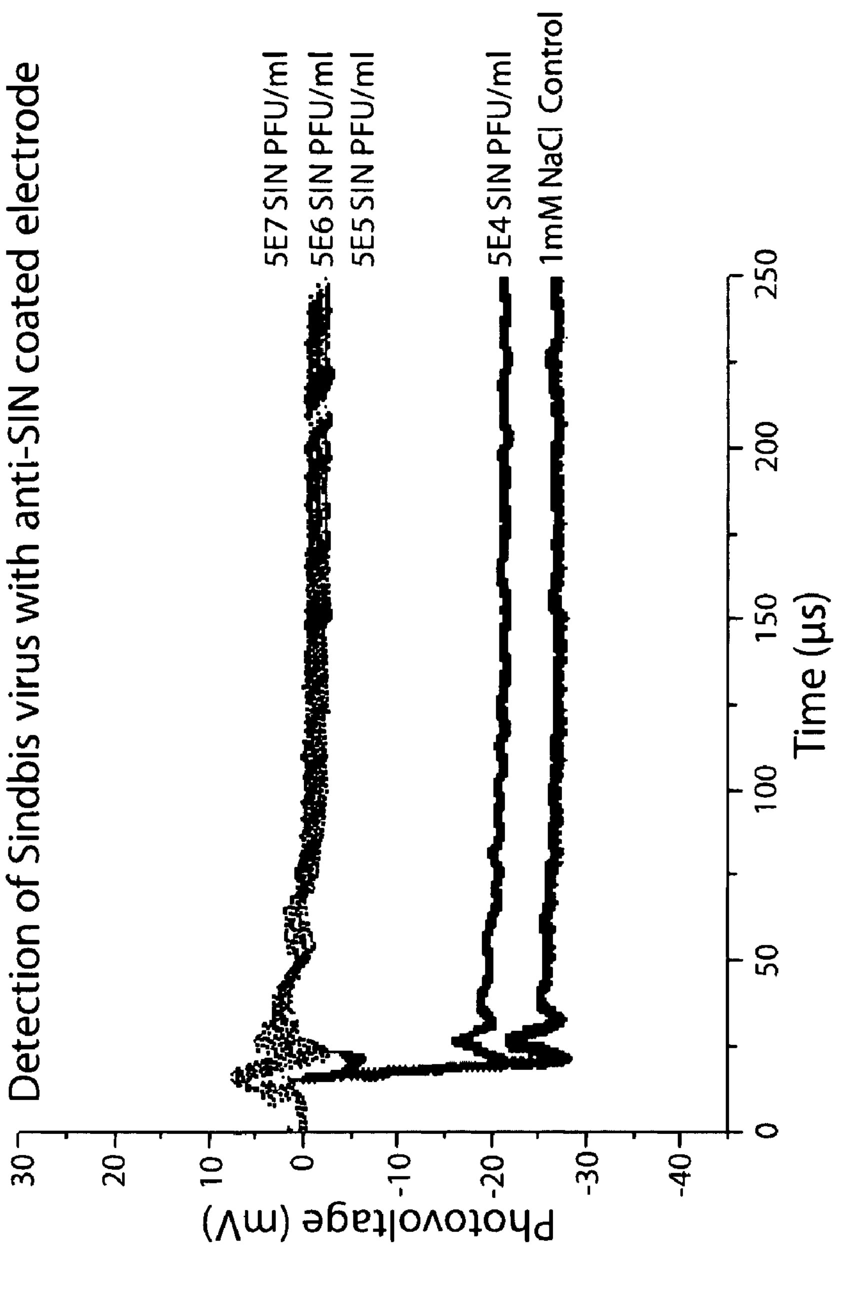
FIG. 12 is a graph showing photovoltage traces for an electrode coated with polyclonal anti-Sindbis antibody (anti- SIN) subsequently exposed to increasing concentrations (i.e., plaque forming units [PFU] per milliliter) of Sindbis virus in test solutions of 1 mM NaCl according to principles of the invention.

FIG. 12 is a graph showing photovoltage traces for an electrode coated with polyclonal anti-Sindbis antibody (anti-SIN) subsequently exposed to increasing concentrations (i.e., plaque forming units [PFU] per milliliter) of Sindbis virus in test solutions of 1 mM NaCl according to principles of the invention. As shown, all photovoltages include initial oscillations from radio frequency noise known to skilled artisans. The photovoltages with no Sindbis virus (i.e., the control) are the largest and negative. Increasing Sindbis virus titer reduces this negative amplitude to effectively saturate at the higher titer shown, demonstrating excellent sensitivity at the lower titer values. Sample dilution, shorter exposure times and possibly different attachment factors could be used for expanding the range.

Figure 13:
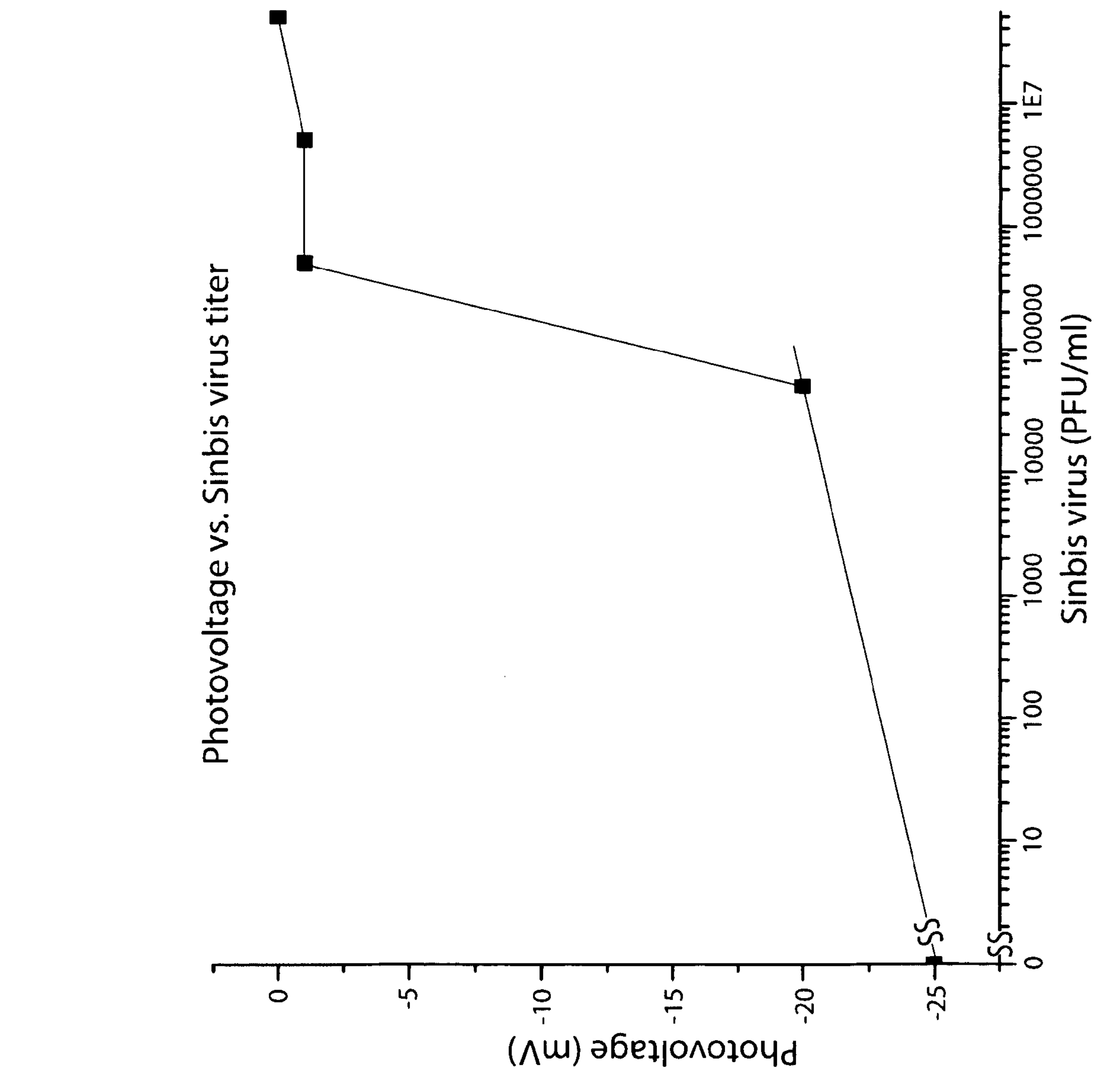
FIG. 13 is a graph showing photovoltage magnitude against Sindbis virus concentration for an electrode coated with anti-SIN subsequently exposed to increasing concentrations of Sindbis virus in test solutions of 1 mM NaCl according to principles of the invention.

FIG. 13 is a graph showing photovoltage magnitude against Sindbis virus concentration for an electrode coated with anti-SIN subsequently exposed to increasing concentrations of Sindbis virus in test solutions of 1 mM NaCl according to principles of the invention. Although a log format is used for the graph, titer value for the left-most point is zero. Therefore, the line extending from that left-most point and the abscissa are broken and an initial numerical value of 1 on the logarithmic abscissa is replaced with a zero. As shown, photovoltage increases with concentration of the analyte (i.e., Sindbis virus). A narrow range of photovoltages covers a wide range of bacterial concentrations. This allows sensing equipment to be adapted to sense a relatively narrow range of photovoltages (e.g., from −10 to +10 mV) to be used for a wide range of analyte concentrations, and for a wide range of analyte-attachment factor combinations.

Figure 14:
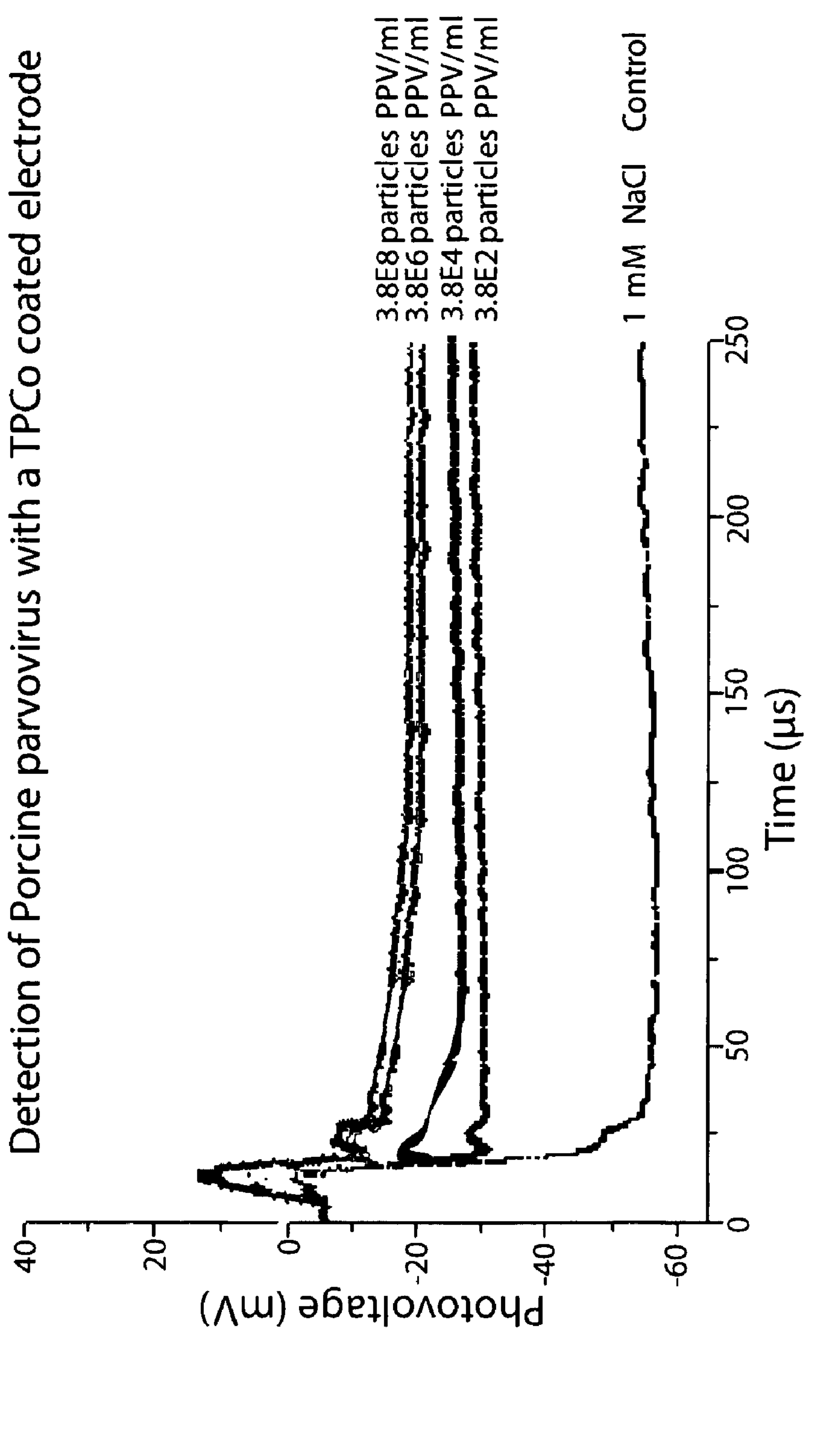
FIG. 14 is a graph showing photovoltage traces for an electrode coated with 5,10,15,20 Tetra(4pyridyl)-21H, 23H porphyrin (TPCo) subsequently exposed to increasing concentrations (i.e., i.e., particles per milliliter, where particles refers to plaque forming units and non-infective virus particles combined) of *Porcine parvovirus* (PPV) in test solutions of 1 mM NaCl according to principles of the invention.

FIG. 14 is a graph showing photovoltage traces for an electrode coated with 5,10,15,20 Tetra(4pyridyl)-21H, 23H porphyrin (TPCo) subsequently exposed to increasing concentrations (i.e., particles per milliliter, where particles refers to plaque forming units and non-infective virus particles combined) of *Porcine parvovirus* (PPV) in test solutions of 1 mM NaCl according to principles of the invention. As shown, all photovoltages include initial oscillations from radio frequency noise known to skilled artisans. The photovoltages with no PPV (i.e., the control) are the largest and negative. Increasing PPV titer reduces this negative amplitude to effectively saturate at the higher titer shown, demonstrating excellent sensitivity at the lower titer values. Sample dilution, shorter exposure times and possibly different attachment factors could be used for expanding the range.

Figure 15:
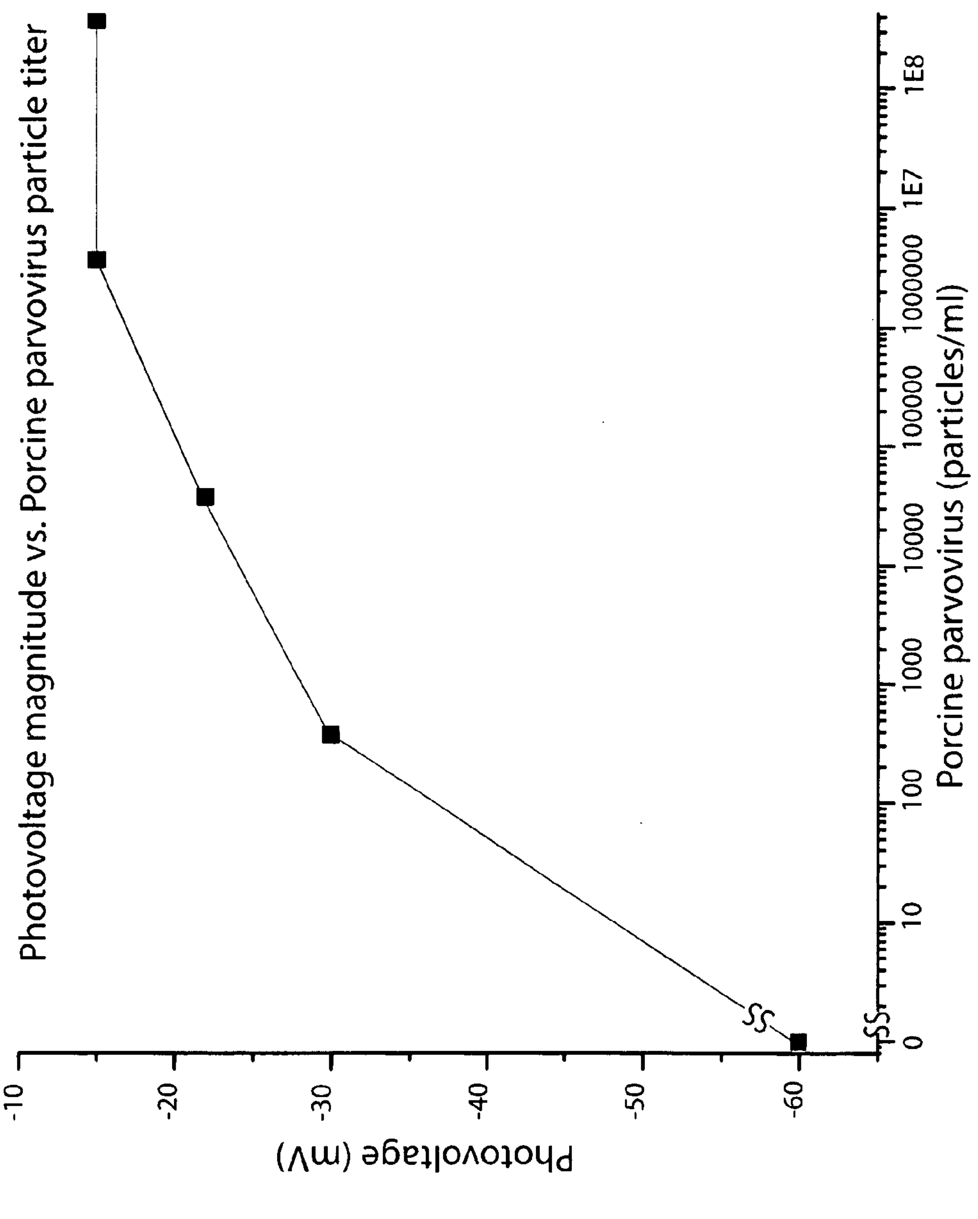
FIG. 15 is a graph showing photovoltage magnitude against PPV concentration for an electrode coated with TPCo subsequently exposed to increasing concentrations of PPV in test solutions of 1 mM NaCl according to principles of the invention.

FIG. 15 is a graph showing photovoltage magnitude against PPV concentration for an electrode coated with TPCo subsequently exposed to increasing concentrations of PPV in test solutions of 1 mM NaCl according to principles of the invention. Although a log format is used for the graph, titer value for the left-most point is zero. Therefore, the line extending from that left-most point and the abscissa are broken and an initial numerical value of 1 on the logarithmic abscissa is replaced with a zero. As shown, photovoltage increases with concentration of the analyte (i.e., PPV). A narrow range of photovoltages covers a wide range of bacterial concentrations. This allows sensing equipment to be adapted to sense a relatively narrow range of photovoltages (e.g., from −10 to +10 mV) to be used for a wide range of analyte concentrations, and for a wide range of analyte-attachment factor combinations.

Figure 16:
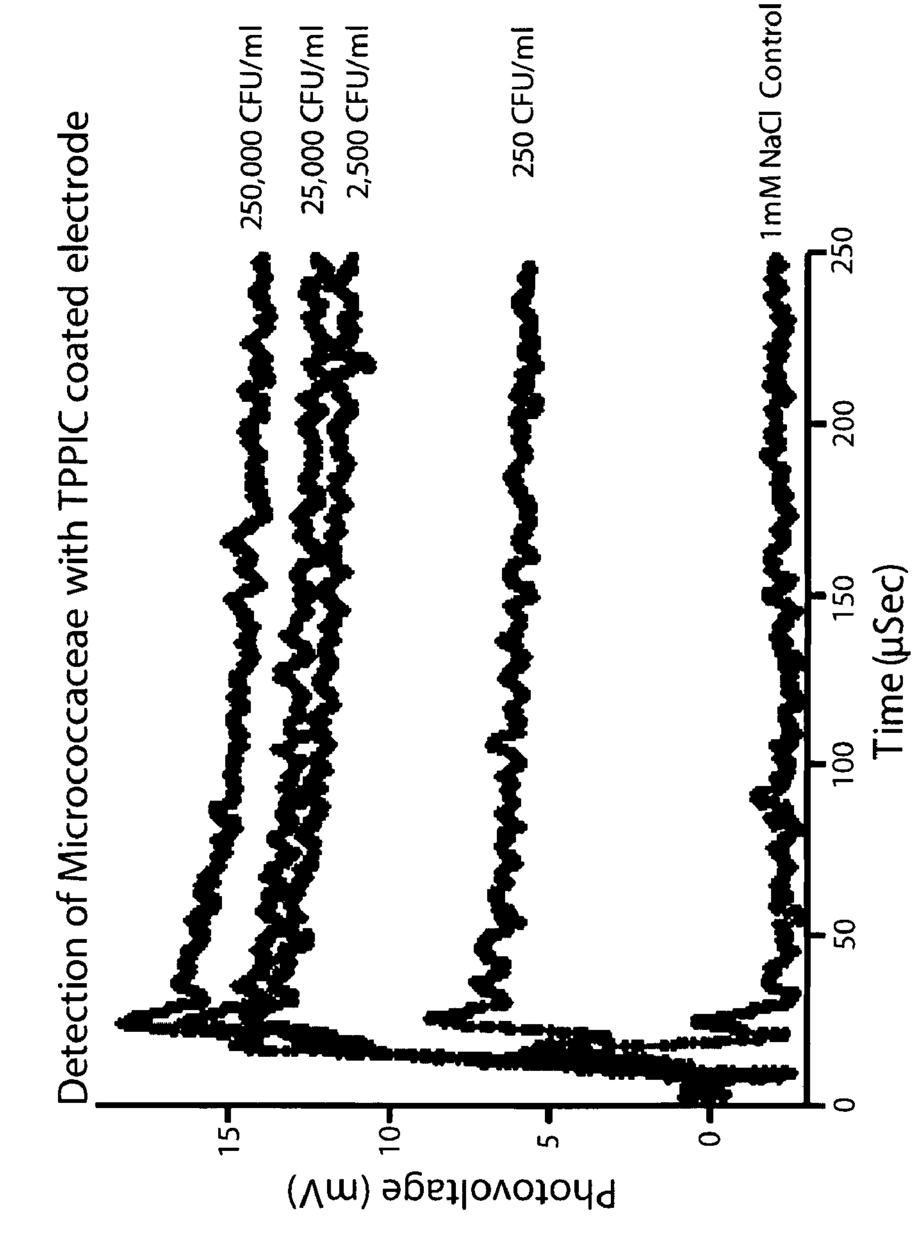
FIG. 16 is a graph showing photovoltage traces for an electrode coated with TPPIC subsequently exposed to increasing concentrations (i.e., CFU per milliliter) of *Micrococcaceae* in test solutions of 1 mM NaCl according to principles of the invention.

FIG. 16 is a graph showing photovoltage traces for an electrode coated with TPPIC subsequently exposed to increasing concentrations (i.e., CFU per milliliter) of *Micrococcaceae* in test solutions of 1 mM NaCl according to principles of the invention. As shown, all photovoltages include initial oscillations from radio frequency noise known to skilled artisans. The photovoltages with no *Micrococcaceae* (i.e., the control) are the lowest and initially negative, but becomes positive with increased positive amplitude with the presence of increased *Micrococcaceae* titer. Increasing *Micrococcaceae* titer increases the positive amplitude to effectively saturate at the higher titer shown, demonstrating excellent sensitivity at the lower titer values. Sample dilution, shorter exposure times and possibly different attachment factors could be used for expanding the range.

A system and method according to principles of the invention offers several advantages over the known prior art. As a result of binding of the attachment factor onto the electrode and the formation of a functional group comprising the attachment factor and a microbial organism, there results a change in electrical response of the electrodes which simultaneously provides an indication of the presence and concentration of said microbial organism in the electrolytic medium. The construction of the system (i.e., a titer meter) is simple, resulting in a cost effective and reliable apparatus. A titer meter according to principles of the invention may be portable or a stationary unit configured to simultaneously run tests on a plurality of test specimens. The system and method enable detection of a wide range of microbial organisms, including virus. The system and method also enable determining concentrations in near real-time, without the requirement to grow micro-organisms.

Illustratively, a system and method according to principles of the invention is useful for detecting and quantitating an agent in a sample, such as an aquatic sample, a food sample, lab stock culture or a blood sample. The determination may be carried out by one of two modes to be referred to herein as the "direct mode" and the "indirect mode." In the direct mode, the analyte is in the electrolyte medium used in the cuvette 115. In the indirect mode, the analyte is in a sample into which the electrode assembly 125 is dipped for a time determined by test protocol and then the electrode assembly 125 is placed in the cuvette 115 with other electrolyte.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A system for detecting the presence and concentration of a microbial organism on an electrode submerged in an electrolytic solution through measured photo-induced interfacial voltages, said system including an electrometer configured to measure photo-induced interfacial voltages;

an electrode assembly comprising a substrate and at least one electrode on a surface of the substrate, said at least one electrode being electrically coupled to the electrometer;

a tissue culture adhesive thin film applied to an exposed surface of the at least one electrode;

an attachment factor applied to the tissue culture adhesive thin film, said attachment factor being effective for interaction with the microbial organism;

a microbial organism physically applied to the attachment factor;

a transparent vessel for containing the electrolytic solution, said electrode assembly configured for placement of the at least one electrode in the transparent vessel; and a light source configured to controllably produce a flash of activating light directed through the transparent vessel at the electrode, said flash of activating light being configured to cause a sensible photo-induce interfacial voltage at the at least one electrode when the at least one electrode with the applied attachment factor is exposed to said flash of activating light while submerged in the electrolytic solution.

2. A system for detecting the presence and concentration of a microbial organism on an electrode submerged in an electrolytic solution according to claim 1, wherein the light source is a source of ultraviolet light and the flash of activating light is a flash of ultraviolet activating light.

3. A system for detecting the presence and concentration of a microbial organism on an electrode submerged in an electrolytic solution according to claim 1, wherein the at least one electrode comprises platinum.

4. A system for detecting the presence and concentration of a microbial organism on an electrode submerged in an electrolytic solution according to claim 1, wherein the at least one electrode comprises a plurality of electrodes and the electrode assembly further comprises at least one ground.

5. A system for detecting the presence and concentration of a microbial organism on an electrode submerged in an electrolytic solution according to claim 1, wherein the electrometer configured to measure photo-induced interfacial voltages comprises an amplifier and a processor operably coupled to the electrode assembly, said processor being configured to compare a measured photo-induced interfacial voltage with a predetermined photo-induced interfacial voltage corresponding to a determined analyte and titer.

6. A system for detecting the presence and concentration of a microbial organism on an electrode submerged in an electrolytic solution according to claim 1, wherein the microbial organism is a virus.

7. A system for detecting the presence and concentration of a microbial organism on an electrode submerged in an electrolytic solution according to claim 1, wherein the electrode assembly is configured to produce and the electrometer is configured to measure photo-induced interfacial voltages between +10 mV and −10 mV in less than 500 μs after said at least one electrode with the applied attachment factor, tissue culture adhesive and microbial organism is exposed to said flash of activating light.

* * * * *